(12) United States Patent
Yan

(10) Patent No.: US 8,166,617 B2
(45) Date of Patent: May 1, 2012

(54) DEVICE FOR ORGANIZING AND MAINTAINING THE PATENCY OF LINES

(76) Inventor: Peter Z. Yan, Allston, MA (US)

( * ) Notice: Subject to any disclaimer, the term of this patent is extended or adjusted under 35 U.S.C. 154(b) by 358 days.

(21) Appl. No.: 12/573,580

(22) Filed: Oct. 5, 2009

(65) Prior Publication Data
US 2011/0078879 A1    Apr. 7, 2011

(51) Int. Cl.
*F16G 11/00* (2006.01)
(52) U.S. Cl. ............... 24/132 R; 24/132 WL; 24/133; 24/71 R; 254/394
(58) Field of Classification Search ........... 24/68 A, 24/68 AS, 68 E, 68 R, 68 T, 69 SB, 69 ST, 24/71 R, 71 SB, 71 ST, 71.1, 129 R, 132 R, 24/132 WL, 133; 174/15.5, 60, 88 R, 97, 174/99 R, 113 R, 117 F, 117 FF, 135; 254/388, 254/389, 394, 395, 397, 408, 411; 439/459, 439/498
See application file for complete search history.

(56) References Cited

U.S. PATENT DOCUMENTS

| 1,194,667 | A | * | 8/1916 | Rosenthal | 254/391 |
| 4,470,501 | A | * | 9/1984 | Wilson | 198/810.01 |
| 6,444,903 | B2 | * | 9/2002 | Saeki et al. | 174/480 |

* cited by examiner

*Primary Examiner* — Robert J Sandy
*Assistant Examiner* — Tyler Johnson
(74) *Attorney, Agent, or Firm* — Dana M. Gordon; Foley Hoag LLP

(57) ABSTRACT

One aspect of the invention relates to a device that efficiently folds and organizes tubing and cords while not compromising their function. In certain embodiments, the device provides dynamic length adjustment in the form to reducing line length, and the device organizes the lines in parallel, making it easier to identify their connections.

28 Claims, 14 Drawing Sheets

DEVICE FOR ORGANIZING AND MAINTAINING THE PATENCY OF LINES

BACKGROUND

Patients in hospital units are typically connected to an assortment of pumps and monitoring devices via myriad tubing and cords. These tubing and cords easily tangle and intertwine when the patients move, leaving a jumbled mass. The two primary reasons behind the tangling of these tubing and cords lie within the standardized length and packing of these lines. Lines are manufactured in standardized lengths, and cannot be dynamically changed. Therefore, in the hospital environment healthcare workers are often forced to use lines that are too long. Furthermore, due to the coiled packaging of the lines, some retain a coiling conformation when lengthened, akin to a telephone cord. Hence, the lines are easily tangled and difficult to untangle. When the lines tangle, they limit patient mobility, complicate patient monitoring and intravenous (IV) drug and fluid delivery, both of which create a patient safety issue. The healthcare worker is then forced to spend considerable amounts of time untangling the cords, a laborious process which consumes time that the worker would have otherwise spent administering actual healthcare to the patient.

For example, a typical patient in a post-operation recovery unit after coronary artery bypass graft will at a minimum have cords attached to them for monitoring ECGs, non-invasive blood pressure, and blood oxygen saturation. The patient will typically also have more than one intravenous line, an arterial line, and perhaps even a peripherally inserted catheter. Furthermore, any one of these lines could have multiple lines piggy-backed onto them. Additionally, there is usually another line delivering oxygen to the patient's nasal cannula. So for this patient, there are at minimum seven different lines that can tangle. All of these lines have significant slack, to give the patient some range of motion, but all this extra length only facilitates tangling. Most problematic are the intravenous, arterial, and peripherally inserted lines. Once the IV lines become tangled, it is essential that they be untangled for the healthcare worker to ascertain which line delivers which drug and is connected to which corresponding pump so that proper medication and dosing can be administered to the patient. Finally, in addition to patients moving their limbs or adjusting their posture, patients are generally moved from bed to chair and vice versa every two to three hours, they also typically ambulate every four hours, and patients may also be transported for diagnostic tests. Each time the patient moves, the lines tangle and must be untangled.

SUMMARY

One aspect of the invention relates to devices which address the prevalent issue of tangled lines at the patient bedside in a hospital unit, facilitating patient care by both decreasing or preventing line tangling, and providing line organization. In certain embodiments, the device consists of mobile, modular units that fold the lines without introducing tension as well as providing convenience of movement for both the healthcare worker and the patient. In certain embodiments, sinusoidal folding of a line allows for dynamic length adjustment of the lines as well as removal of the coiling property of IV lines due to their packaging and long-term storage. Furthermore, in certain embodiments, the stacking feature of the device also allows for parallel organization of the lines.

For example, one aspect of the invention relates to a device comprising a first arm comprising a proximal end and a distal end; a second arm comprising a proximal end and a distal end' a pin pivotally coupling the proximal end of the first arm and the proximal end of the second arm, the first arm and the second arm being configured for rotation about the pin between an open position and a closed position, wherein in the open position the distal end of the first arm and the distal end of the second arm are at opposite ends of the folding unit, and in the closed position the distal end of the first arm and the distal end of the second arm are adjacent to each other; a wheel configured and positioned for rotation around the pin; a first protrusion on the first arm; a first indentation on the second arm; wherein said first protrusion is complimentary to said first indentation, and said first protrusion fits into said first indentation on the second arm when the device is in the closed position; a first longitudinal groove on the first arm and a second longitudinal groove on the second arm, wherein said first longitudinal groove and said second longitudinal groove are on the same side of the device when the device is in the open position; a first u-shaped piece positioned at or near the end of the first longitudinal groove and sized to house a line; a second u-shaped piece positioned at or near the end of the second longitudinal groove and sized to house a line; wherein the first u-shaped piece and the second u-shaped piece are sized so that one u-shaped piece fits inside the other u-shaped piece while leaving a space for a line to move there through; a third piece positioned between the first u-shaped piece and the wheel and slidably connected to the first longitudinal groove, comprising a first curved notch that is sized to house and attach to a line; a fourth piece positioned between the second piece and the wheel and slidably connected to the second longitudinal groove, comprising a second curved notch that is sized to house and attach to a line; a second protrusion on the first arm; and a second indentation on the first arm; wherein said second protrusion is complimentary to said second indentation, and said second protrusion and said second indentation are located on opposite sides of the first arm.

Additional aspects, embodiments, and advantages of the invention are discussed below in detail.

Importantly, in the Figures the dimensions of the device are shown in relative terms. The specific dimensions depends on how much folding is required and the diameter of the line to be folded. For example, the lengths of parts I and II (FIG. 5b) and the diameter of the attachment groove in Part V (FIG. 5e) may vary. The length of parts I and II determine the amount of folding created by one folding unit. In certain embodiments, a reasonable length for part I and part II would be about 5 cm, which allows a unit fold of about 10 cm. If more folding is desired, more units can be attached in series. The diameter of the attachment groove for Part V varies depending on that of the line; a typical IV line has a diameter of about 0.5 cm and lines of different patient monitors can be between about 1 cm and about 2 cm in diameter. In certain embodiment, to create a firm attachment, the groove's diameter should be no more than about 1-2% smaller than that of the diameter of the line.

DETAILED DESCRIPTION

Figure 1A:
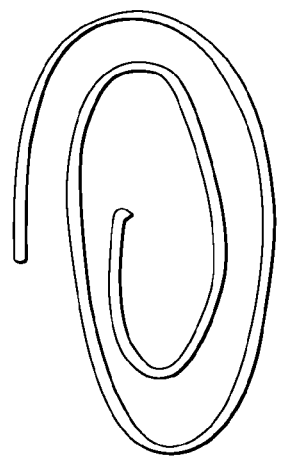
FIG. 1A depicts radial coiling of lines, as found in typical packaging.
Figure 1B:
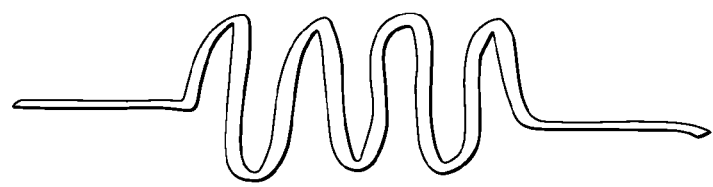
FIG. 1B depicts sinusoidal folding of the line as the method of length reduction by a folding unit.

One aspect of the invention relates to a device that, instead of coiling a line radially, folds a line in a sinusoidal fashion, thereby providing length reduction of the line (see FIG. 1). In certain embodiments, the device maintains patency of the line. In certain embodiments, the device is modular and can fold the line, reducing its length, any number of times. In certain embodiments, the device can organize multiple lines in parallel. In certain embodiments, the device does not add tension on the line when it is folded. In certain embodiments, the device allows for free linear movement of line when it is folded. In certain embodiments, the device easily switches between the folded and unfolded state.

Definitions

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein a "line" refers to cord or tubing, including cords from electrical monitoring devices and drug or fluid delivery tubing from intravenous (IV) delivery pumps. In addition, IV, arterial and peripherally inserted line (catheter) will be collectively referred to herein as "IV" lines.

Devices

One aspect of the invention relates to a folding unit, comprising:

a first arm comprising a proximal end and a distal end;

a second arm comprising a proximal end and a distal end;

a pin pivotally coupling the proximal end of the first arm and the proximal end of the second arm, the first arm and the second arm being configured for rotation about the pin between an open position and a closed position, wherein in the open position the distal end of the first arm and the distal end of the second arm are at opposite ends of the folding unit, and in the closed position the distal end of the first arm and the distal end of the second arm are adjacent to each other;

a wheel configured and positioned for rotation around the pin;

a first protrusion on the first arm;

a first indentation on the second arm;

wherein said first protrusion is complimentary to said first indentation, and said first protrusion fits into said first indentation on the second arm when the device is in the closed position;

a first longitudinal groove on the first arm and a second longitudinal groove on the second arm, wherein said first longitudinal groove and said second longitudinal groove are on the same side of the device when the device is in the open position;

a first u-shaped piece positioned at or near the end of the first longitudinal groove and sized to house a line;

a second u-shaped piece positioned at or near the end of the second longitudinal groove and sized to house a line;

wherein the first u-shaped piece and the second u-shaped piece are sized so that one u-shaped piece fits inside the other u-shaped piece while leaving a space for a line to move there through;

a third piece positioned between the first u-shaped piece and the wheel and slidably connected to the first longitudinal groove, comprising a first curved notch that is sized to house and attach to a line;

a fourth piece positioned between the second piece and the wheel and slidably connected to the second longitudinal groove, comprising a second curved notch that is sized to house and attach to a line;

a second protrusion on the first arm; and a second indentation on the first arm;

wherein said second protrusion is complimentary to said second indentation, and said second protrusion and said second indentation are located on opposite sides of the first arm.

In certain embodiments, the present invention relates to any one of the aforementioned folding units, wherein the length of the first arm is between about 1 cm and about 10 cm; and the length of the second arm is between about 1 cm and about 10 cm.

In certain embodiments, the present invention relates to any one of the aforementioned folding units, wherein the length of the first arm is between about 2.5 cm and about 7.5 cm in length; and the length of the second arm is between about 2.5 cm and about 7.5 cm.

In certain embodiments, the present invention relates to any one of the aforementioned folding units, wherein the length of the first arm is about 5 cm; and the length of the second arm is about 5 cm.

In certain embodiments, the present invention relates to any one of the aforementioned folding units, wherein the first protrusion fits snugly into the first indentation. In all embodiments described herein wherein one protrusion fits into an indentation, other means by which one may affix one piece to another, or one unit to another, such as magnets or Velcro®, may also be used.

In certain embodiments, the present invention relates to any one of the aforementioned folding units, wherein the first protrusion is circular; and the first indentation is circular.

In certain embodiments, the present invention relates to any one of the aforementioned folding units, further comprising a line.

In certain embodiments, the present invention relates to any one of the aforementioned folding units, wherein the line has a diameter between about 0.1 cm to about 3 cm.

In certain embodiments, the present invention relates to any one of the aforementioned folding units, wherein the line has a diameter between about 0.5 cm and about 2.0 cm.

In certain embodiments, the present invention relates to any one of the aforementioned folding units, wherein the first curved notch has a diameter of about 0.5% to about 3% less than the diameter of the line; and the second curved notch has a diameter of about 0.5% to about 3% less than the diameter of the line In certain embodiments, the present invention relates to any one of the aforementioned folding units, wherein the first u-shaped piece is slidably connected to the first longitudinal groove; and the second u-shaped piece is slidably connected to the second longitudinal groove.

In certain embodiments, the present invention relates to any one of the aforementioned folding units, wherein the second protrusion fits snugly into the second indentation.

In certain embodiments, the present invention relates to any one of the aforementioned folding units, wherein the second protrusion is rectangular; and the second indentation is rectangular.

Another aspect of the invention relates to a device for organizing and maintaining the patency of lines comprising a plurality of folding unit; wherein each folding unit comprises:

a first arm comprising a proximal end and a distal end;

a second arm comprising a proximal end and a distal end;

a pin pivotally coupling the proximal end of the first arm and the proximal end of the second arm, the first arm and the second arm being configured for rotation about the pin between an open position and a closed position, wherein in the open position the distal end of the first arm and the distal end of the second arm are at opposite ends of the folding unit, and in the closed position the distal end of the first arm and the distal end of the second arm are adjacent to each other;

a wheel configured and positioned for rotation around the pin;

a first protrusion on the first arm;

a first indentation on the second arm;

wherein said first protrusion is complimentary to said first indentation, and said first protrusion fits into said first indentation on the second arm when the device is in the closed position;

a first longitudinal groove on the first arm and a second longitudinal groove on the second arm, wherein said first longitudinal groove and said second longitudinal groove are on the same side of the device when the device is in the open position;

a first u-shaped piece positioned at or near the end of the first longitudinal groove and sized to house a line;

a second u-shaped piece positioned at or near the end of the second longitudinal groove and sized to house a line;

wherein the first u-shaped piece and the second u-shaped piece are sized so that one u-shaped piece fits inside the other u-shaped piece while leaving a space for a line to move there through;

a third piece positioned between the first u-shaped piece and the wheel and slidably connected to the first longitudinal groove, comprising a first curved notch that is sized to house and attach to a line;

a fourth piece positioned between the second piece and the wheel and slidably connected to the second longitudinal groove, comprising a second curved notch that is sized to house and attach to a line;

a second protrusion on the first arm; and a second indentation on the first arm;

wherein said second protrusion is complimentary to said second indentation, and said second protrusion and said second indentation are located on opposite sides of the first arm; and each folding unit is connected to an adjacent folding units by either the joining of its second protrusions to the second indentation on another folding unit or by the joining of its first u-shaped piece or second u-shaped piece with its complementary u-shaped piece on another folding unit.

In certain embodiments, the present invention relates to any one of the aforementioned devices, wherein the plurality of folding units are all in the closed position.

In certain embodiments, the present invention relates to any one of the aforementioned devices, wherein the length of the first arm of each folding unit is between about 1 cm and about 10 cm; and the length of the second arm of each folding unit is between about 1 cm and about 10 cm.

In certain embodiments, the present invention relates to any one of the aforementioned devices, wherein the length of the first arm of each folding unit is between about 2.5 cm and about 7.5 cm; and the length of the second arm of each folding unit is between about 2.5 cm and about 7.5 cm.

In certain embodiments, the present invention relates to any one of the aforementioned devices, wherein the length of the first arm of each folding unit is about 5 cm; and the length of the second arm of each folding unit is about 5 cm.

In certain embodiments, the present invention relates to any one of the aforementioned devices, wherein the first protrusion of each folding unit fits snugly into the corresponding first indentation on the same folding unit.

In certain embodiments, the present invention relates to any one of the aforementioned devices, wherein the first protrusion of each folding unit is circular; and the first indentation of each folding unit is circular.

In certain embodiments, the present invention relates to any one of the aforementioned devices, further comprising a line that passes through and over the plurality of folding units.

In certain embodiments, the present invention relates to any one of the aforementioned devices, wherein the line has a diameter between about 0.1 cm to about 3 cm.

In certain embodiments, the present invention relates to any one of the aforementioned devices, wherein the line has a diameter between about 0.5 cm and about 2.0 cm.

In certain embodiments, the present invention relates to any one of the aforementioned devices, wherein the first curved notch of each folding unit has a diameter of about 0.5% to about 3% less than the diameter of the line; and the second curved notch of each folding unit has a diameter of about 0.5% to about 3% less than the diameter of the line.

In certain embodiments, the present invention relates to any one of the aforementioned devices, wherein the first u-shaped piece of each folding unit is slidably connected to the first longitudinal groove on the same folding unit; and the second u-shaped piece of each folding unit is slidably connected to the second longitudinal groove on the same folding unit.

In certain embodiments, the present invention relates to any one of the aforementioned devices, wherein the second protrusion fits snugly into the second indentation.

In certain embodiments, the present invention relates to any one of the aforementioned devices, wherein the second protrusion is rectangular; and the second indentation is rectangular.

Exemplification

The invention now being generally described, it will be more readily understood by reference to the following, which is included merely for purposes of illustration of certain aspects and embodiments of the present invention, and is not intended to limit the invention.

Figure 2:
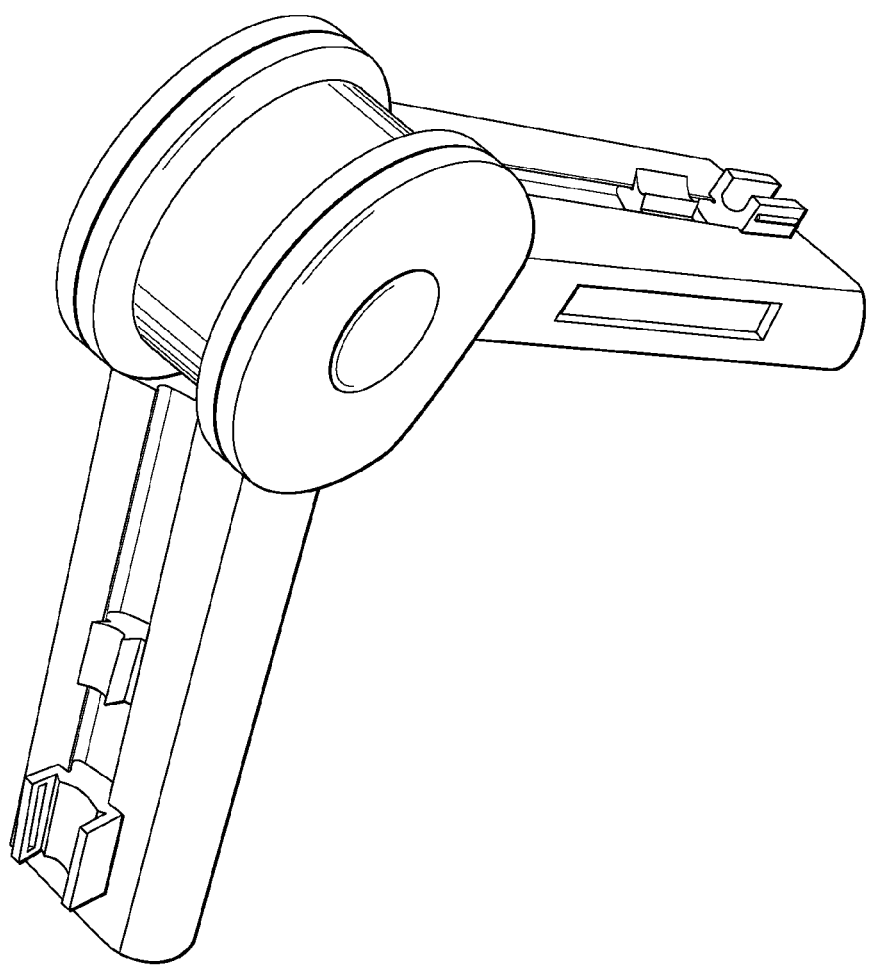
FIG. 2 depicts a single folding unit.
Figure 3:
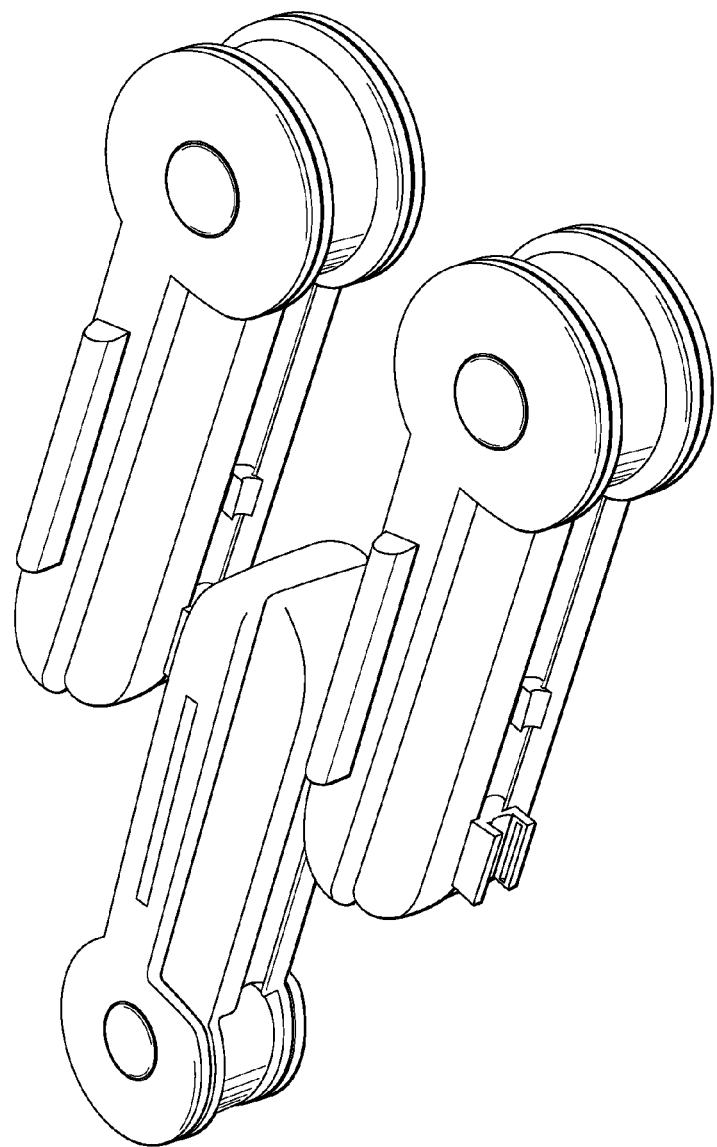
FIG. 3 depicts three folding units connected in series.
Figure 4:
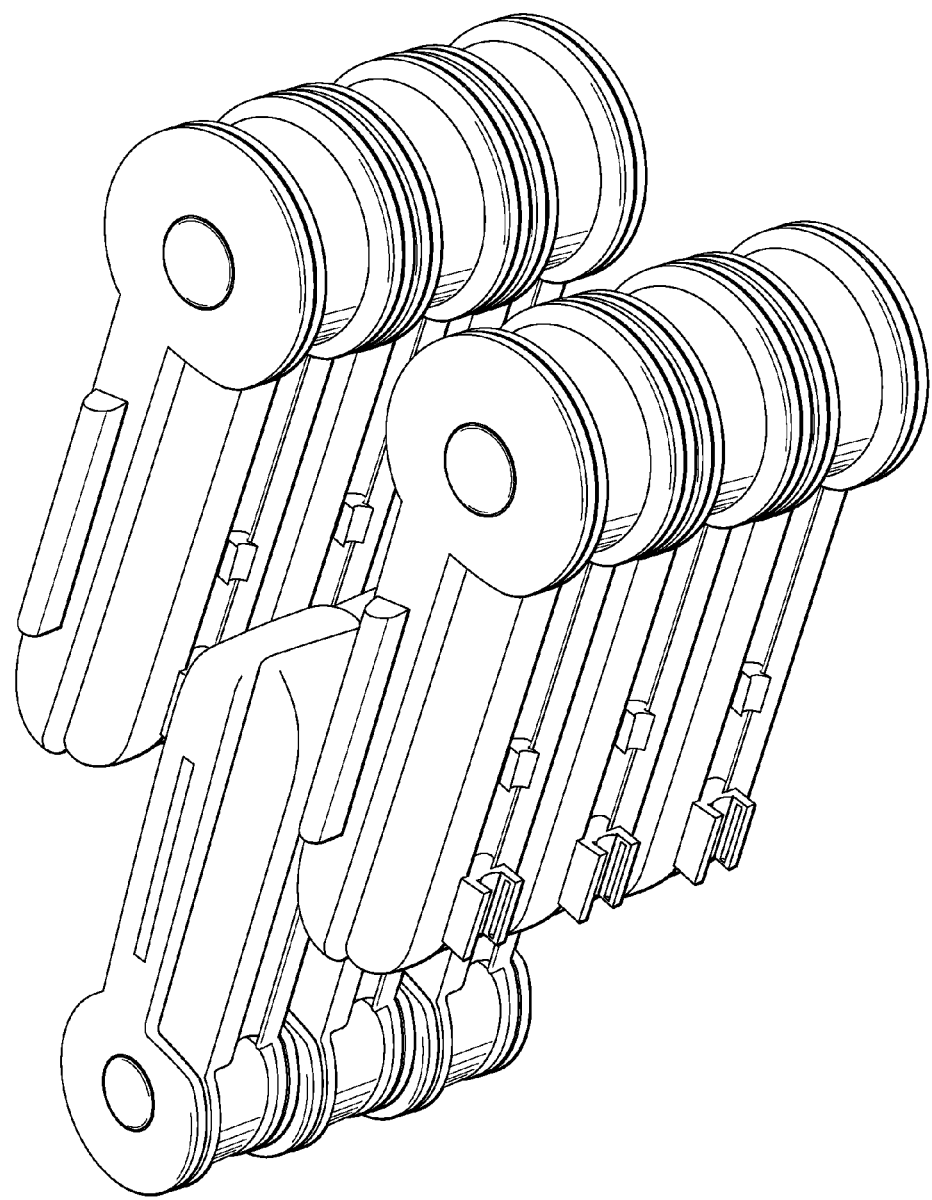
FIG. 4 depicts three sets of three folding units stacked together.

FIG. 2 depicts a folding unit that folds a cord to a specific length. Several of these folding units can be attached in series to allow any number of folds in the line (see FIG. 3). The folding units can also be stacked in parallel so that lines can be organized in parallel fashion (see FIG. 4).

Figure 5A:
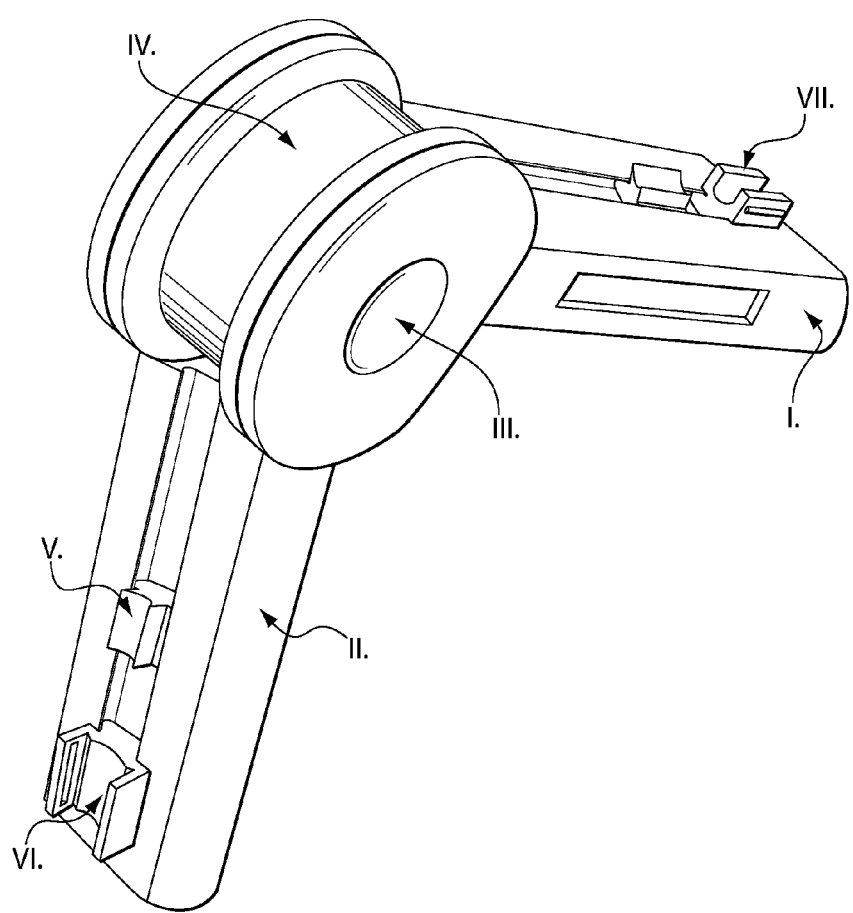
FIG. 5A depicts individual parts of a folding unit when assembled (viewed from top right).
Figure 5B:
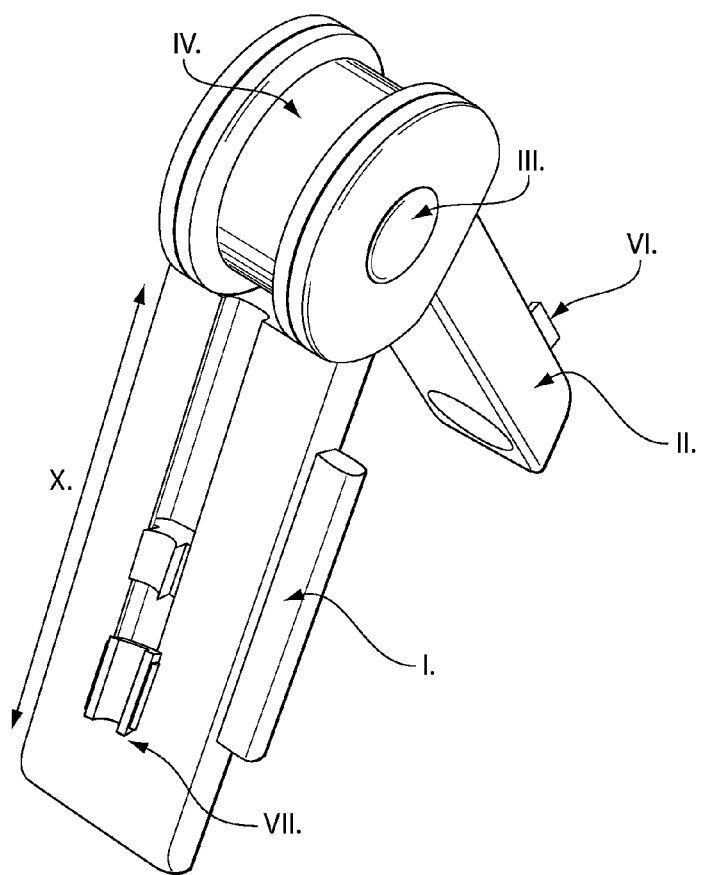
FIG. 5B depicts individual parts of a folding unit when assembled (viewed from right). X denotes the length of Part I, with is identical to the length of Part II.
Figure 5C:
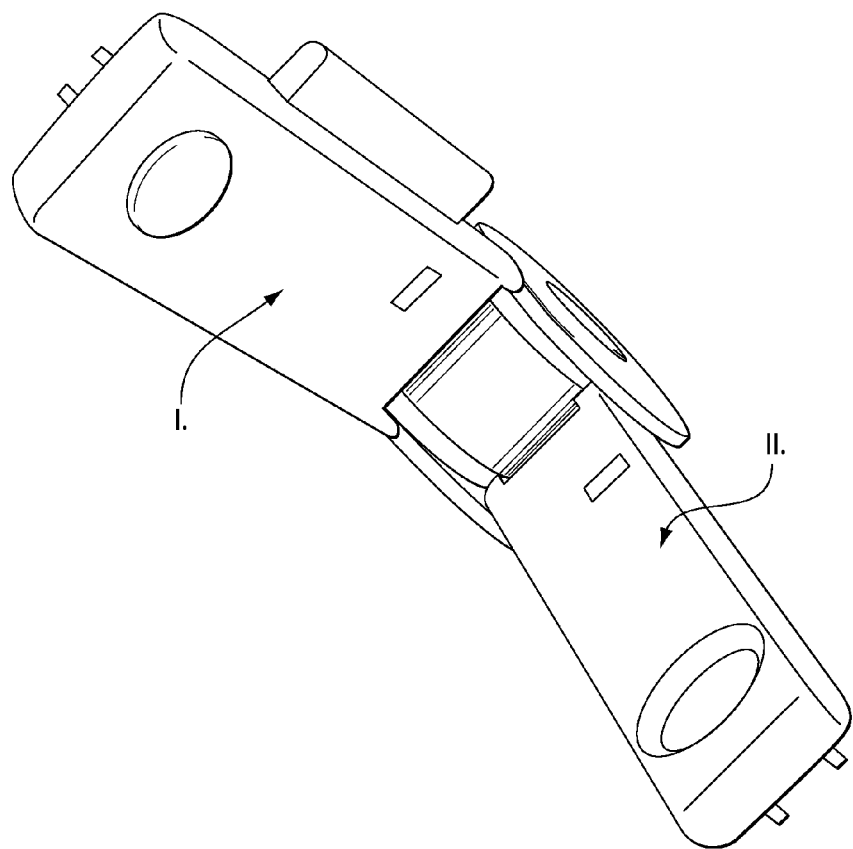
FIG. 5C depicts a folding unit when assembled viewed from bottom.
Figure 5D:
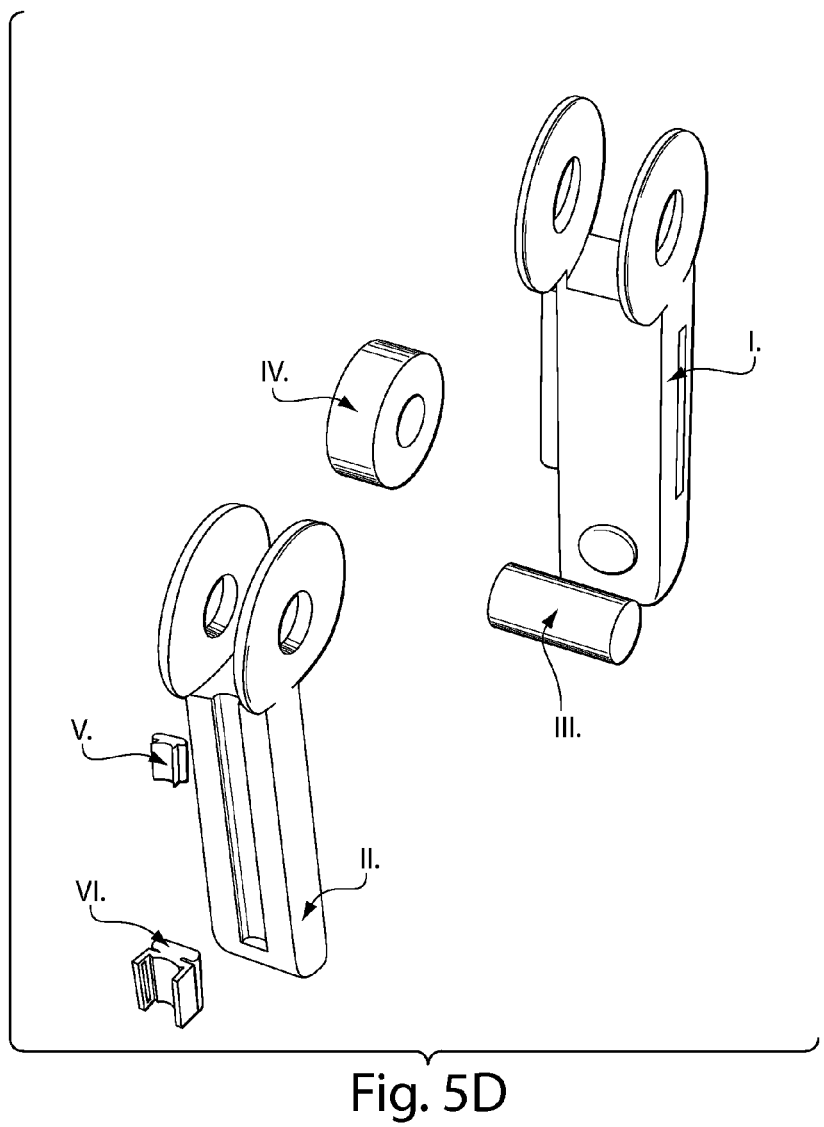
FIG. 5D depicts a disassembled view of a folding unit.

FIGS. 5A-F depict a folding unit consists of several parts. As shown in FIG. 5A, parts I and II are the main folding pieces which rotate like a hinge on part III. Part I has a protrusion and corresponding a slot on its sides which allow folding units to stack on top of one another (see FIGS. 4, 5a and 5b). In certain embodiments, at the bottom of part I is a round protrusion that fit into a corresponding slot at the bottom of part II (FIG. 5c); this allows the folding unit to maintain its position when folded.

As shown, the folding unit comprises a freely rotating wheel (part IV) that uses part III as an axle.

Figure 5E:
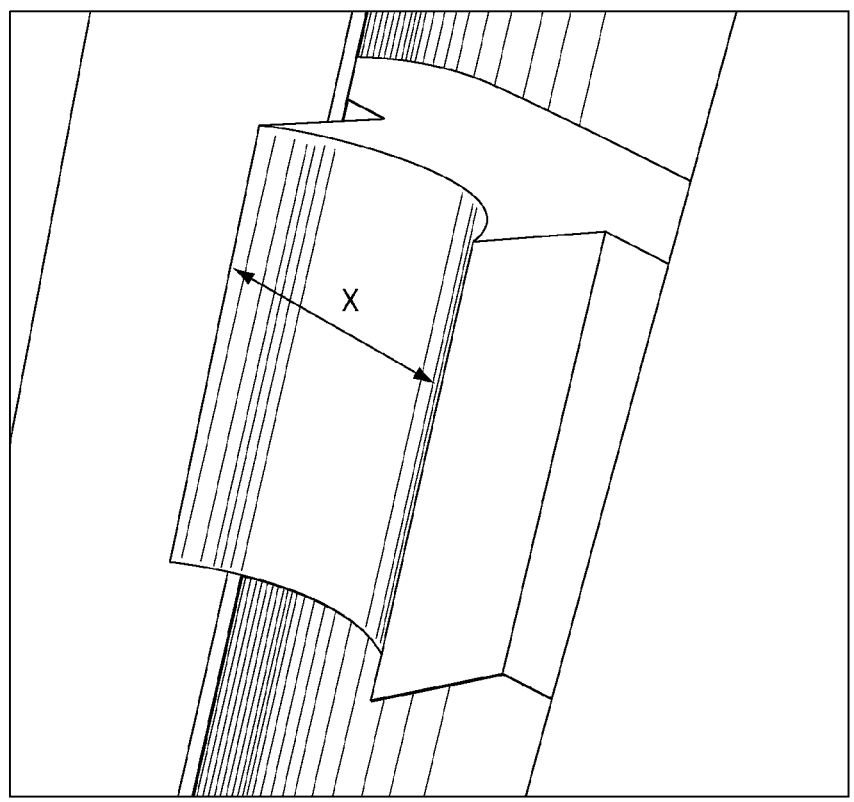
FIG. 5E depicts a close up view of Part V. "X" denotes the diameter of the attachment groove.

In addition, two pieces (denoted as part V) attach in the grooves in parts I and II and freely slide up and down. These pieces also have a curved notch that snugly fit and attach to the line that would be folded (FIG. 5e). Although the inside of the attachment groove of part V has been depicted as smooth, it can also be roughened to allow for better attachment to the line.

Figure 5F:
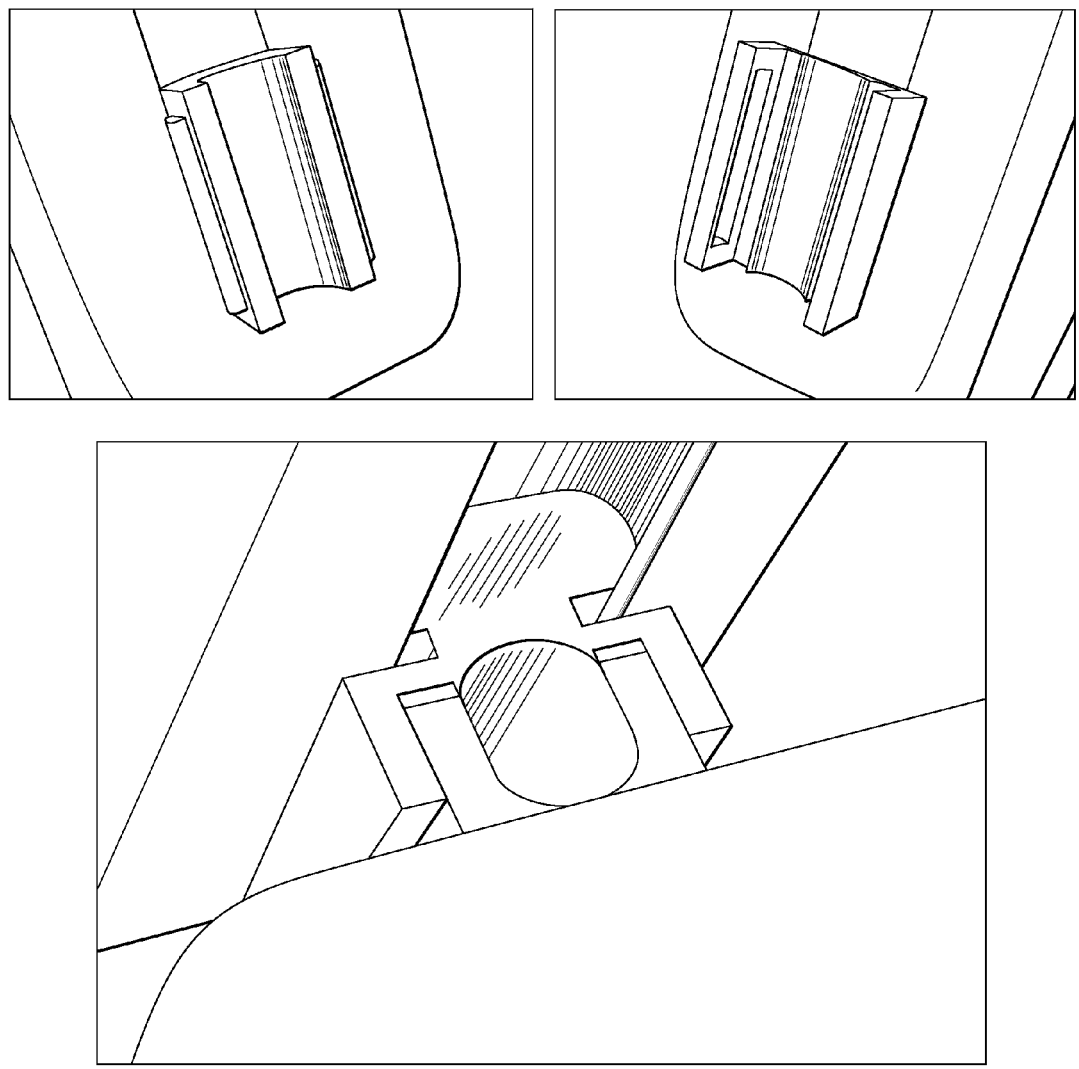
FIG. 5F depicts a close up view of Parts VI and VII and when they latch on to one another.

In addition, the folding unit comprises two complementary pieces (parts VI and VII) that clasp on to each other, while forming a space for the line to move through (FIG. 5f).

Figure 6A:
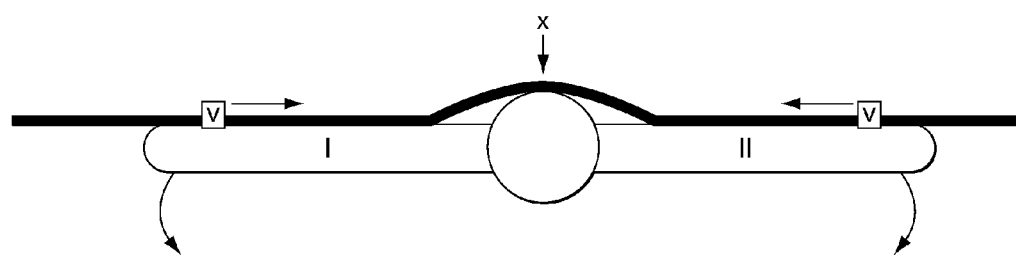
FIG. 6 depicts the folding process by one folding unit. Note that Part V slides up as the folding proceeds. "X" marks the focal point of tension on the line if Part V were immobile
Figure 6B:
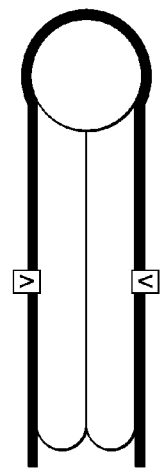

Before folding, the line lies over the device as shown in FIG. 6a. The two pieces of part V firmly attach to the line. As the device folds the line, parts V slide up in their grooves in parts I and II (FIG. 6b). If the movement of parts V was not allowed, as the line folded, tension would build at the apex of folding, which could deform or even rupture the line.

Figure 7A:
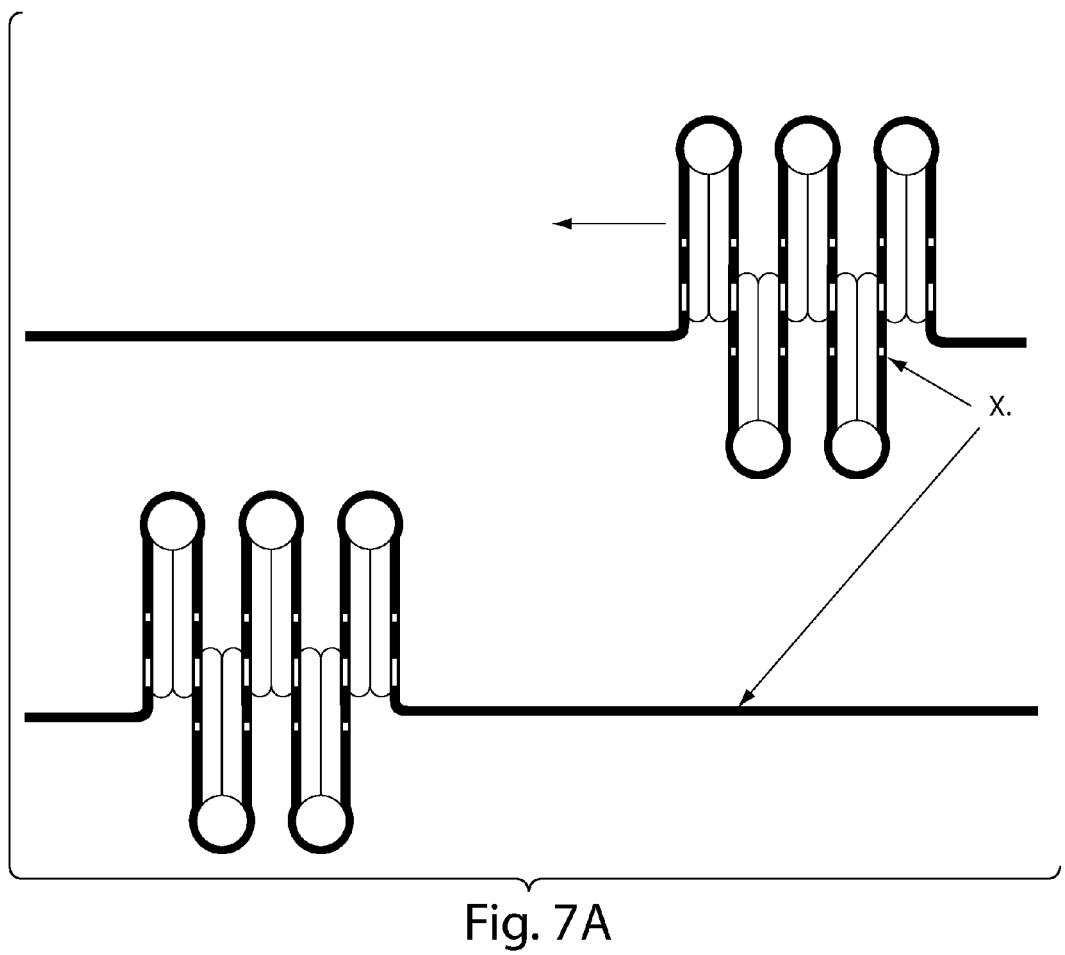
FIG. 7A depicts the linear movement of a series of folding units on a line. "X" denotes a point of examination, such an occlusion. After the folding units shift the left, the point of examination is readily revealed.
Figure 7B:
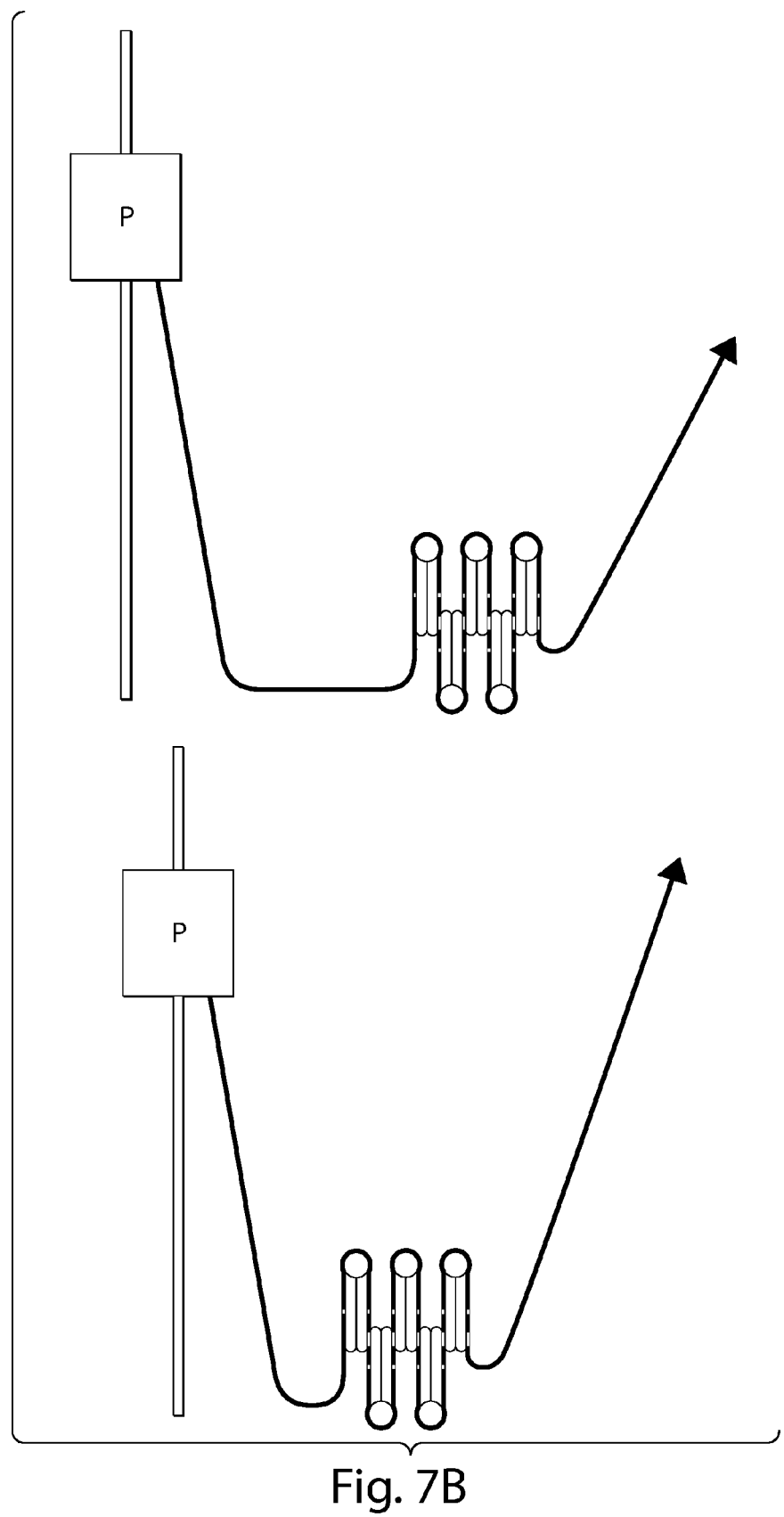
FIG. 7B depicts how as a patient lifts ups on a line, a device shifts, still remaining at the lowest point, not acting as a dead weight. "P" denotes an IV pump.

When several folding units are connected in series and folded, the freely rotating wheel in each unit allows the folded section of the line to freely move along the line. This provides the healthcare worker the ability to move the device so that part of the line may be examined, for example to check for air bubbles in the line (FIG. 7a). Furthermore, because the device freely move on the line, the patient does not always need to lift the device every time he tugs on the line, as the device will simply move and remain at the lowest point (FIG. 7b), so that it is not a source of dead weight that would otherwise add tension on the line.

Figure 8:
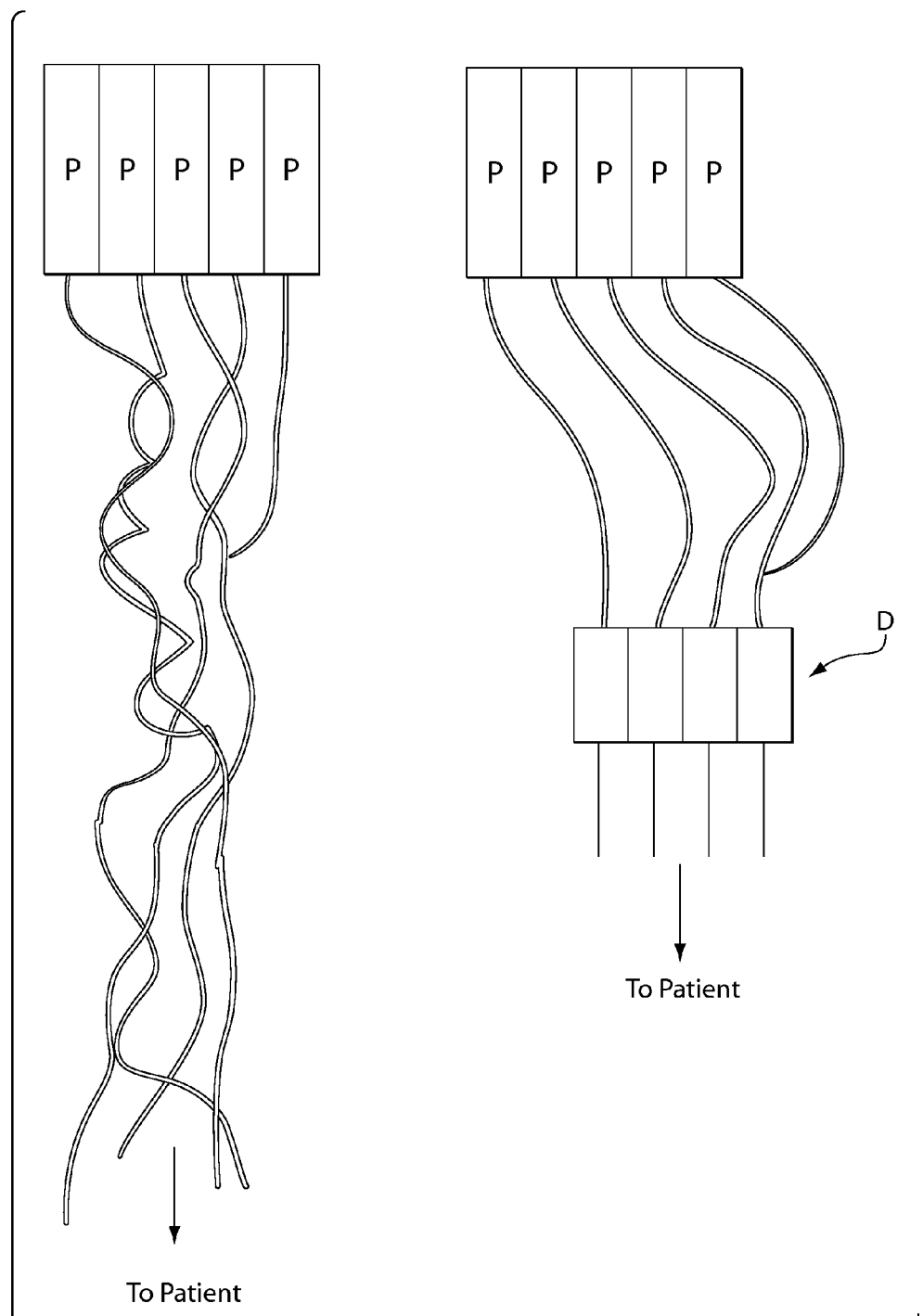
FIG. 8 depicts a typical tangle of IV lines (left) and IV lines after they have been folded and arranged in parallel by folding units (right). "D" denotes a series of folding units stacked in parallel and "P" denotes IV pumps. Note that the IV line on the far right is piggy backed into its neighbor.

Finally, a protrusion on each unit fits into a complementary groove on another identical unit so that the series of folding units stack (FIG. 4), which allow multiple lines to be organized in parallel (FIG. 8).

Incorporation By Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

I claim:

1. A folding unit, comprising:
   a first arm comprising a proximal end and a distal end;
   a second arm comprising a proximal end and a distal end;
   a pin pivotally coupling the proximal end of the first arm and the proximal end of the second arm, the first arm and the second arm being configured for rotation about the pin between an open position and a closed position, wherein in the open position the distal end of the first arm and the distal end of the second arm are at opposite ends of the folding unit, and in the closed position the distal end of the first arm and the distal end of the second arm are adjacent to each other;
   a wheel configured and positioned for rotation around the pin;
   a first protrusion on the first arm;
   a first indentation on the second arm;
   wherein said first protrusion is complimentary to said first indentation, and said first protrusion fits into said first indentation on the second arm when the device is in the closed position;
   a first longitudinal groove on the first arm and a second longitudinal groove on the second arm, wherein said first longitudinal groove and said second longitudinal groove are on the same side of the device when the device is in the open position;
   a first u-shaped piece positioned at or near the end of the first longitudinal groove and sized to house the line;
   a second u-shaped piece positioned at or near the end of the second longitudinal groove and sized to house the line;
   wherein the first u-shaped piece and the second u-shaped piece are sized so that one u-shaped piece fits inside the other u-shaped piece while leaving a space for the line to move there through;
   a third piece positioned between the first u-shaped piece and the wheel and slidably connected to the first longitudinal groove, comprising a first curved notch that is sized to house and attach to the line;
   a fourth piece positioned between the second piece and the wheel and slidably connected to the second longitudinal groove, comprising a second curved notch that is sized to house and attach to the line;
   a second protrusion on the first arm; and
   a second indentation on the first arm;
   wherein said second protrusion is complimentary to said second indentation, and said second protrusion and said second indentation are located on opposite sides of the first arm.

2. The folding unit of claim 1, wherein the length of the first arm is between about 1 cm and about 10 cm; and the length of the second arm is between about 1 cm and about 10 cm.

3. The folding unit of claim 1, wherein the length of the first arm is between about 2.5 cm and about 7.5 cm; and the length of the second arm is between about 2.5 cm and about 7.5 cm.

4. The folding unit of claim 1, wherein the length of the first arm is about 5 cm; and the length of the second arm is about 5 cm.

5. The folding unit of claim 1, wherein the first protrusion fits snugly into the first indentation.

6. The folding unit of claim 1, wherein the first protrusion is circular; and the first indentation is circular.

7. The folding unit of claim 1, further comprising the line.

8. The folding unit of claim 7, wherein the line has a diameter between about 0.1 cm to about 3 cm.

9. The folding unit of claim 7, wherein the line has a diameter between about 0.5 cm and about 2.0 cm.

10. The folding unit of claim 7, wherein the first curved notch has a diameter of about 0.5% to about 3% less than the diameter of the line; and the second curved notch has a diameter of about 0.5% to about 3% less than the diameter of the line.

11. The folding unit of claim 1, wherein the first u-shaped piece is slidably connected to the first longitudinal groove; and the second u-shaped piece is slidably connected to the second longitudinal groove.

12. The folding unit of claim 1, wherein the second protrusion fits snugly into the second indentation.

13. The folding unit of claim 1, wherein the second protrusion is rectangular; and the second indentation is rectangular.

14. A device for organizing and maintaining the patency of lines comprising a plurality of folding units; wherein each folding unit comprises:
    a first arm comprising a proximal end and a distal end;
    a second arm comprising a proximal end and a distal end;
    a pin pivotally coupling the proximal end of the first arm and the proximal end of the second arm, the first arm and the second arm being configured for rotation about the pin between an open position and a closed position, wherein in the open position the distal end of the first arm and the distal end of the second arm are at opposite ends of the folding unit, and in the closed position the distal end of the first arm and the distal end of the second arm are adjacent to each other;
    a wheel configured and positioned for rotation around the pin;
    a first protrusion on the first arm;
    a first indentation on the second arm;
    wherein said first protrusion is complimentary to said first indentation, and said first protrusion fits into said first indentation on the second arm when the device is in the closed position;
    a first longitudinal groove on the first arm and a second longitudinal groove on the second arm, wherein said first longitudinal groove and said second longitudinal groove are on the same side of the device when the device is in the open position;
    a first u-shaped piece positioned at or near the end of the first longitudinal groove and sized to house a line;
    a second u-shaped piece positioned at or near the end of the second longitudinal groove and sized to house the line;
    wherein the first u-shaped piece and the second u-shaped piece are sized so that one u-shaped piece fits inside the other u-shaped piece while leaving a space for the line to move there through;
    a third piece positioned between the first u-shaped piece and the wheel and slidably connected to the first longitudinal groove, comprising a first curved notch that is sized to house and attach to the line;
    a fourth piece positioned between the second piece and the wheel and slidably connected to the second longitudinal groove, comprising a second curved notch that is sized to house and attach to the line;
    a second protrusion on the first arm; and
    a second indentation on the first arm;
    wherein said second protrusion is complimentary to said second indentation, and said second protrusion and said second indentation are located on opposite sides of the first arm; and
    each folding unit is connected to an adjacent folding units by either the joining of its second protrusions to the second indentation on another folding unit or by the joining of its first u-shaped piece or second u-shaped piece with its complementary u-shaped piece on another folding unit.

15. The device of claim 14, wherein the plurality of folding units are all in the closed position.

16. The device of claim 14, wherein the length of the first arm of each folding unit is between about 1 cm and about 10 cm; and the length of the second arm of each folding unit is between about 1 cm and about 10 cm.

17. The device of claim 14, wherein the length of the first arm of each folding unit is between about 2.5 cm and about 7.5 cm; and the length of the second arm of each folding unit is between about 2.5 cm and about 7.5 cm.

18. The device of claim 14, wherein the length of the first arm of each folding unit is about 5 cm; and the length of the second arm of each folding unit is about 5 cm.

19. The device of claim 14, wherein the first protrusion of each folding unit fits snugly into the corresponding first indentation on the same folding unit.

20. The device of claim 14, wherein the first protrusion of each folding unit is circular; and the first indentation of each folding unit is circular.

21. The device of claim 14, further comprising the line that passes through and over the plurality of folding units.

22. The folding unit of claim 21, wherein the line has a diameter between about 0.1 cm to about 3 cm.

23. The folding unit of claim 21, wherein the line has a diameter between about 0.5 cm and about 2.0 cm.

24. The folding unit of claim 21, wherein the first curved notch of each folding unit has a diameter of about 0.5% to about 3% less than the diameter of the line; and the second curved notch of each folding unit has a diameter of about 0.5% to about 3% less than the diameter of the line.

25. The folding unit of claim 14, wherein the first u-shaped piece of each folding unit is slidably connected to the first longitudinal groove on the same folding unit; and the second u-shaped piece of each folding unit is slidably connected to the second longitudinal groove on the same folding unit.

26. The folding unit of claim 14, wherein the second protrusion fits snugly into the second indentation.

27. The folding unit of claim 14, wherein the second protrusion is rectangular; and the second indentation is rectangular.

28. The device of claim 14, further comprising a plurality of lines that passes through and over the plurality of folding units.

* * * * *